United States Patent [19]

Gauthier-Lafaye et al.

[11] 4,353,844
[45] Oct. 12, 1982

[54] PREPARATION OF ANHYDRIDES BY CARBONYLATION OF ESTERS

[75] Inventors: Jean Gauthier-Lafaye, Lyons; Robert Perron, Charly, both of France

[73] Assignee: Rhone-Poulenc Industries, Paris, France

[21] Appl. No.: 281,179

[22] Filed: Jul. 7, 1981

[30] Foreign Application Priority Data

Sep. 11, 1980 [FR] France .................. 80 19875

[51] Int. Cl.³ .................. C07C 51/56; C07C 53/12
[52] U.S. Cl. .................. 260/549; 260/546
[58] Field of Search .................. 260/549, 546

[56] References Cited

U.S. PATENT DOCUMENTS

| | | | |
|---|---|---|---|
| 4,002,678 | 1/1977 | Naglieri et al. | 260/549 |
| 4,115,444 | 9/1978 | Rizkalla | 260/549 |
| 4,239,698 | 12/1980 | Isshiki et al. | 260/546 |
| 4,241,219 | 12/1980 | Wan | 260/549 |
| 4,246,195 | 1/1981 | Szecsi | 260/549 |
| 4,251,458 | 2/1981 | Pugach | 260/546 |

*Primary Examiner*—Johnnie R. Brown
*Assistant Examiner*—Frederick V. Pepper
*Attorney, Agent, or Firm*—Burns, Doane, Swecker & Mathis

[57] ABSTRACT

Carboxylic acid anhydrides are prepared by carbonylating a carboxylic acid ester in liquid phase, in an essentially anhydrous reaction medium including a sulfone reaction solvent, and in the presence of a catalytically effective amount of (i) nickel and an alkyl or acyl iodide promoter therefor, and (ii) a co-catalyst which comprises at least one alkali or alkaline earth metal salt, or quaternary ammonium or phosphonium iodide.

The subject process is well adapted, e.g., for the preparation of acetic anhydride by carbonylation of methyl acetate.

30 Claims, No Drawings

PREPARATION OF ANHYDRIDES BY CARBONYLATION OF ESTERS

BACKGROUND OF THE INVENTION

1. Field of the Invention

The present invention relates to the preparation of carboxylic acid anhydrides, and, more especially, to the preparation of carboxylic acid anhydrides, notably acetic anhydride, by carbonylation of a carboxylic acid ester.

2. Description of the Prior Art

It is well known to this art that, e.g., acetic anhydride can be prepared by carbonylation of methyl acetate, under relatively severe conditions of pressure, in the presence of nickel complexes of the formula $$[A_4M]_2NiX_4$$

in which X represents a bromine or iodine atom, M represents a phosphorus or nitrogen atom and A is, for example, a lower alkyl radical (compare U.S. Pat. No. 2,729,651). These complexes, which are obtained by reacting nickel halides with quaternary phosphonium or ammonium halides, can be employed in this form in the subject reaction, or, alternatively, they can be formed in situ. However, the efficiency of this type of process is low, despite the high pressures used.

More recently, catalyst systems have been proposed which make it possible to carbonylate methyl acetate under less severe pressure conditions. Thus, U.S. Pat. No. 4,002,678 describes the carbonylation of methyl acetate in the presence of nickel, chromium, methyl iodide and a phosphine (or an amine), under a pressure of less than 70 bars.

Parallel thereto, it has also been shown that chromium is not necessary in a process of the aforesaid type if the reaction is carried out in the presence of carboxylic acid solvent (compare published French Patent Application No. 2,408,571). Nevertheless, the industrial-scale development of these recent techniques, the value of which is not disputed in principle, is jeopardized on the one hand by the instability and the cost of the phosphines or amines required to carry them out, and on the other hand by the relatively low efficiency of the catalyst systems in question.

SUMMARY OF THE INVENTION

Accordingly, a major object of the present invention is the provision of an improved process for the preparation of carboxylic acid anhydrides, notably lower alkanoic acid anhydrides, and especially acetic anhydride, by carbonylation of carboxylic acid esters in the presence of nickel and at least one iodine-containing promoter, with good productivity, under relatively mild pressure conditions, while at the same time avoiding those disadvantages and drawbacks to date characterizing the state of this art.

Briefly, the present invention features an improved process for the carbonylation of carboxylic acid esters in liquid phase, in an essentially anhydrous medium, in the presence of an effective amount of nickel, at least one alkyl or acyl iodide, a sulfone as solvent, and at least one co-catalyst selected from among the alkali metal salts, alkaline earth metal salts, quaternary ammonium iodides and quaternary phosphonium iodides.

DETAILED DESCRIPTION OF THE INVENTION

More particularly according to the present invention, the subject process can be conveniently represented by the following equation:

$$R-C-OR + CO \rightarrow (RCO)_2O \tag{I}$$

in which R represents an alkyl radical having at most 12 carbon atoms, or a radical $C_6H_5-C_xH_{2x}-$, with x being an integer ranging from 1 to at most 6.

R is preferably an alkyl radical having from 1 to 4 carbon atoms, such as methyl, ethyl, n-propyl, isopropyl, n-butyl, secondary butyl or tert.-butyl.

By the expression "essentially anhydrous medium" there is intended a medium which contains only traces of water originating from the reactants and/or from the components of the catalyst system, if it is desired to use commercially available products.

The process according to the invention requires the presence of any catalytically effective amount of nickel. Any source of nickel can be used within the scope of the present process. Thus, the nickel can be introduced in metallic form (for example, Raney nickel) or in any other convenient form. The following are exemplary of those nickel compounds which can be used to carry out the present process: nickel carbonate, oxide, hydroxide, halides, in particular the iodide, and carboxylates, in particular the acetate. Nickel carbonyl is also suitable. It is preferred to use Raney nickel, nickel iodide, nickel acetate and nickel carbonyl.

The amount of nickel is not critical. The proportion of nickel, which influences the reaction rate, is determined as a function of the reaction rate which is considered to be suitable, taking account of the other reaction parameters. In general, an amount ranging from 5 to 2,000 milligram atoms of nickel per liter of solution provides satisfactory results. The reaction is preferably carried out with an amount of from 20 to 1,000 milligram atoms of nickel per liter.

In conducting the process of the present invention, the presence is also required of at least one alkyl or acyl iodide, namely, at least one compound of the formula R'I (or R'COI), in which R' is defined as was R above, it further being possible for R' and R to be identical or different. It is preferred to use alkyl iodides having at most 4 carbon atoms, and more particularly methyl or ethyl iodide.

It is not necessary for this type of component of the catalyst system to be introduced initially. It is of course possible for free iodine or hydriodic acid to be introduced initially.

It has also been determined that, in the reaction medium, the alkali metal (or alkaline earth metal) iodides can be considered as precursors of the alkyl (or acyl) iodides. Lithium, sodium and potassium iodides are suitable for carrying out the subject process. Lithium iodide is particularly effective.

Typically, the amount of alkyl (or acyl) iodide, or of their precursor(s), is such that the molar ratio I/Ni ranges from 1 to 100. This ratio is advantageously a value ranging from about 3 to about 50.

One of the essential characteristics of the present invention is the use of a sulfone as the reaction solvent.

The sulfones which are employed within the scope of the present invention are preferably those represented by the formula (I) below:

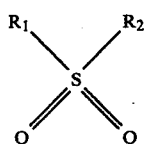 (I)

in which $R_1$ and $R_2$, which are identical or different, represent alkyl radicals having at most 4 carbon atoms, it being possible for $R_1$ and $R_2$ to together form a single divalent alkylene or alkenylene radical containing from 3 to 6 carbon atoms (for example, a tetramethylene or hexamethylene radical) and, if appropriate, 1 or 2 ethylenic double bonds, and it also being possible for said radical to bear 1 to 3 alkyl substituents having from 1 to 4 carbon atoms.

A first type of sulfones which are suitable for carrying out the present process comprises the dialkyl sulfones, namely, the sulfones of the above formula (I) in which $R_1$ and $R_2$ are identical and preferably represent linear alkyl radicals having at most 4 carbon atoms.

A second category of sulfones which are particularly suitable for carrying out the present process comprises tetramethylenesulfone, 3-methyltetramethylenesulfone, 2,4-dimethyltetramethylenesulfone, and mixtures thereof.

Typically, the amount of sulfone constitutes at least 10% by volume of the reaction medium; good results are obtained if the amount employed is on the order of 20% to 75% (by volume) of sulfone.

A second essential parameter of the present process is the use of at least one co-catalyst selected from among alkali metal salts, alkaline earth metal salts, quaternary ammonium iodides and quaternary phosphonium iodides.

The alkali metal salts and alkaline earth metal salts which are useful within the scope of the present invention correspond to the following formula (II):

$$M_b{}^{a+}X_c{}^{m-} \qquad (II)$$

in which a, m, b and c are integers equal to 1 or 2, the respective values of which are selected such as to satisfy the condition $a \times b = m \times c$ and, if a and m are identical, b and c are equal to 1, M represents a lithium, sodium, potassium, cesium, rubidium, calcium or magnesium atom and $X^{m-}$ is an anion selected from the group comprising: $OH^-$, $Cl^-$, $Br^-$, $I^-$, $CO_3{}^=$, $NO_3{}^-$, $R''-O^-$ and $R''-CO-O^-$, $R''$ being defined exactly as was R above and it being possible for $R''$ and R is be identical or different.

Among these compounds, the alkali metal salts, and especially the lithium, sodium or potassium salts, are particularly preferred for carrying out the present process.

The precise nature of the anion $X^{m-}$ would not appear to be a fundamental parameter of the subject process. The following are exemplary of alkali metal salts which are suitable for carrying out the present process: LiOH, LiI, NaCl, KBr, NaI, KI, RbI, CsI, NaNO₃, K₂CO₃, Li₂CO₃, CsNO₃, lithium, sodium or potassium acetate, sodium or potassium methylate and sodium, potassium or lithium ethylate. The alkali metal carboxylates ($R''-COOM$), and more particularly the acetates, are convenient to use and in this respect are recommended for carrying out the present invention.

The precise nature of the quaternary ammonium or phosphonium iodides which can be used as co-catalysts is not of fundamental importance within the scope of the present process. The choice from among such compounds is governed more by considerations of a practical nature, such as solubility in the reaction medium, the availability and the convenience of use.

In this respect, preferred is the use of quaternary ammonium or phosphonium iodides in which the cations are represented, respectively, by the following structural formulae (III) and (IV):

$$R_3N^+(R_4)_3 \qquad (III)$$

$$R_3P^+(R_4)_3 \qquad (IV)$$

in which $R_3$ and $R_4$, which are identical or different, represent linear alkyl radicals having at most 4 carbon atoms, it also being possible for $R_4$ to represent a phenyl, tolyl or xylyl radical.

Exemplary of such quaternary ammonium iodides suitable for carrying out the present process are tetramethylammonium, triethylmethylammonium, tributylmethylammonium, tributyl-(n-propyl)-ammonium, tetraethylammonium and tetrabutylammonium iodides.

Exemplary of quaternary phosphonium iodides suitable for carrying out the present process are methyltriphenylphosphonium, ethyltriphenylphosphonium, methyltrixylylphosphonium and methyltributylphosphonium iodides.

It too will be seen that the alkali metal iodides in the process according to the invention can be considered, not only as co-catalysts, but also as precursors of the alkyl (or acyl) iodides mentioned hereinabove. Stated differently, if an alkali metal iodide is introduced into the reaction medium, it is not necessary to add an alkyl (or acyl) iodide and/or one of the co-catalysts defined noted hereinabove.

Of course, within the scope of the present process, it is envisaged to use several co-catalysts from one or another of the categories above defined. Thus, it is foreseen to use an alkali metal iodide and an alkali metal carboxylate, for example, sodium iodide and lithium acetate, or lithium iodide and potassium acetate. Similarly, it is envisaged to use a quaternary phosphonium iodide and an alkali metal carboxylate, for example, methyltriphenylphosphonium iodide and lithium (or sodium) acetate.

Typically, the presence of 0.5 to 50 mols of co-catalyst per gram atom of nickel provides satisfactory results. To carry out the process according to the invention satisfactorily, from 2 to 25 mols of co-catalyst are used per gram atom of nickel.

According to another embodiment of the present process, chromium or a chromium compound can be added to the catalyst system defined above.

The chromium compounds which can be used within the scope of this particular embodiment of the invention, nonetheless an optical embodiment, are preferably chromium hexacarbonyl and the chromium salts having the following formula (V):

$$Cr_n{}^{p+}Y_q{}^{m-} \qquad (V)$$

in which q denotes the ratio $(n \times p)/m$, p is equal to 2, 3, 4 or 6, m is as defined above, n is equal to 1 or 2 and is selected as a function of the respective values of m and p such that q is an integer, and Y is defined exactly as was X in the formula (II), it also being possible for Y to represent an anion $O^=$, $HCOO^-$, $C_2O_4^=$ or $CH_3COCHC(CH_3)O^-$.

Being markedly convenient to use, chromium carboxylates, especially chromium (III) acetate, are especially recommended in this respect.

If it is desired to carry out the subject process consistent with this optional variant, chromium or chromium compounds are used in proportions, relative to the nickel, which are essentially on the same order as those indicated above for the co-catalyst, which is a component of the basic catalyst system.

Basically according to the present invention, carbon monoxide is contacted with an alkyl carboxylate in the presence of (i) a sulfone solvent, and (ii), that catalyst system defined above.

The reaction is carried out in liquid phase under a pressure in excess of atmospheric pressure. Typically, the subject reaction is carried out under a total pressure of more than 15 bars; it serves no purpose to employ pressures as high as 700 bars. To carry out the invention satisfactorily, a total pressure of 25 to 200 bars is recommended.

The reaction temperature is usually above 160° C., but it is not necessary to employ temperatures as high as 300° C. Good results are obtained within the temperature range from 180° to 220° C.

Carbon monoxide is preferably used in essentially pure form, as available commercially. However, the presence of certain impurities, such as carbon dioxide, oxygen, methane and nitrogen, is readily tolerated. The presence of hydrogen is not detrimental, even in relatively large proportions.

Upon completion of the reaction, the carboxylic acid anhydride obtained is separated from the other constituents of the reaction medium by any suitable means, for example, by distillation.

An additional advantage of the present invention is the fact that especially effective catalyst compositions are obtained from very readily accessible species having extremely simple structures.

A first category of catalyst compositions, the use of which constitutes one preferred embodiment of the present invention, includes nickel and an alkali metal iodide, in particular lithium, sodium or potassium iodide, with lithium iodide proving particularly effective.

A second category of catalyst compositions, the use of which constitutes another preferred embodiment of the present invention, includes nickel, an alkyl iodide and an alkali metal carboxylate. The alkyl iodide is advantageously methyl iodide; the alkali metal carboxylate is more particularly an acetate, with lithium acetate being particularly suitable.

A final category of preferred catalyst compositions includes nickel, an alkyl iodide, an alkali metal iodide and an alkali metal carboxylate; methyl iodide, sodium iodide and lithium acetate, together with nickel, circumscribe a particularly effective catalyst composition.

The process according to the invention is especially valuable for the preparation of acetic anhydride from methyl acetate, in a tetramethylenesulfone reaction medium.

In order to further illustrate the present invention and the advantages thereof, the following specific Examples are given, it being understood that same are intended only as illustrative and in nowise limitative.

In said Examples which follow, the following conventions are used:
AcOMe: denotes methyl acetate;
TMS: denotes tetramethylenesulfone;
$Ac_2O$: denotes acetic anhydride;
AcOH: denotes acetic acid;
V: denotes the initial reaction rate, espressed in mols of carbon monoxide absorbed per hour;
RY (%): denotes the number of mols of acetic anhydride formed per 100 mols of methyl acetate introduced;
Pr: denotes productivity with respect of acetic anhydride, expressed in grams per hour and per liter of reaction medium.

EXAMPLE 1

The following materials were introduced into a Hastelloy B-2 autoclave having a capacity of 125 ml:
(i) 25 ml (312 mmols) of methyl acetate;
(ii) 20 ml of tetramethylenesulfone;
(III) 8 mg atoms of nickel, in the form of nickel acetate tetrahydrate;
(iv) 80 mols of methyl iodide; and
(v) 20 mmols of methyltriphenylphosphonium iodide.

After closing the autoclave, a pressure of 40 bars of carbon monoxide was established therein. Shaking by means of a reciprocating system was commenced and the autoclave was heated to 180° C. over the course of about 25 minutes by means of an annular furnace. The pressure in the autoclave was then 46 bars. It was subsequently maintained constant and equal to 70 bars by introducing additional amounts of carbon monoxide. The pressure drop in the high-pressure supply which continuously charged the autoclave was recorded. After a reaction time of two hours at the temperature indicated, the shaking and heating were stopped; the autoclave was cooled and degassed. The resulting reaction mixture was diluted and analyzed by gas chromatography. The results obtained are reported in Table I below.

Control experiment a:
Example I was repeated, the tetramethylenesulfone being replaced by an identical volume of methyl acetate.

Control experiment b:
Example I is repeated, the tetramethylenesulfone being replaced by the same volume of acetic acid.

The results of control experiments a and b are also reported in Table I below, which clearly shows that, in the absence of solvent, the reaction in question does not take place, and that the replacement of the acetic acid by a sulfone makes it possible to markedly increase the rate of carbonylation.

TABLE 1

| EXAMPLE No. | AcOMe ml | Solvent Nature | ml | V | $Ac_2O$ RY (%) | Pr |
|---|---|---|---|---|---|---|
| a | 45 | — | 0 | 0 | 0 | — |
| b | 25 | AcOH | 20 | 0.05 | 18 | 55 |
| 1 | 25 | TMS | 20 | 0.16 | 32 | 110 |

EXAMPLE 2

Example 1 was repeated, but with the methyltriphenylphosphonium iodide being replaced by 40 mmols of sodium iodide.

The results obtained were as follows:
V=0.12
RY=28%
Pr=90 g/hour×liter

EXAMPLE 3

Example 2 was repeated, but with the sodium iodide being replaced by an equivalent amount of lithium acetate.

The results obtained were as follows:
V=0.34
RY=52%
Pr=160 g/hour×liter

Control experiment (c)

Example 3 was repeated, but with the solvent (TMS) being replaced by an equivalent volume of methyl acetate; no absorption of the carbon monoxide occurred.

EXAMPLE 4

Example 2 was repeated, but with 4 mmols of chromium(III) acetate being added to the reaction mass.

The results obtained were as follows:
V=0.27
RY=58%
Pr=180 g/hour×liter

EXAMPLE 5

Example 1 was repeated, but with 4 mmols of chromium (III) acetate being added to the reaction mass.

The results obtained were as follows:
V=0.36
RY=78%
Pr=250 g/hour×liter

EXAMPLE 6

Example 2 was repeated, but with 40 mmols of lithium acetate being added to the reaction mass.

The results obtained were as follows:
V=0.32
RY=71%
Pr=230 g/hour×liter

EXAMPLE 7

Example 1 was repeated, but with 40 mmols of lithium acetate being added to the reaction mass.

The results obtained were as bollows:
V=0.35
RY=65%
Pr=225 g/hour×liter

Control experiment d

Control experiment (a) was repeated, but with 40 mmols of lithium acetate being added to the reaction mass.

The rate (v) was equal to 0.05 and RY was less than 5%.

EXAMPLE 8

Using the equipment and procedure described above, carbon monoxide was reacted with a medium consisting of 30 ml of methyl acetate, 20 ml of tetramethylenesulfone, 120 mmols of sodium iodide and 8 mg atoms of nickel, in the form of nickel acetate tetrahydrate, for two hours, at 180° C., under a total pressure of 70 bars. Upon completion of the experiment, 2.6 g of acetic anydride were determined (RY−7%).

EXAMPLE 9

Using the equipment and procedure described above, carbon monoxide was reacted with a medium consisting of 23 ml of methyl acetate, 20 ml of tetramethylenesulfone, 110 mmols of methyl iodide, 40 mmols of potassium acetate and 16 mmols of nickel acetate tetrahydrate, for 2 hours, under a total pressure of 70 bars, the temperature being only 160° C. Upon completion of the experiment, 1.3 g of acetic anhydride were determined (RY−5%). This amount was considerable, taking into account the low reaction temperature chosen.

EXAMPLE 10

A mixture of carbon monoxide and hydrogen in the molar ratio 2/1 was reacted with a medium consisting of 26 ml of methyl acetate, 20 ml of 2,4-dimethyltetramethylenesulfone, 8 mmols of nickel acetate tetrahydrate, 65 mmols of methyl iodide and 50 mmols of potassium iodide. After a reaction time of 2 hours at 180° C., under a total pressure maintained at 90 bars by introducing additional amounts of carbon monoxide, 6.7 g of acetic anhydride were determined (RY=21%).

Control experiment e

Example 10 was repeated, but with potassium iodide being absent and 5 mmols of nickel iodide hexahydrate being employed. After the experiment had been conducted for 3 hours, 30 minutes, no absorption of the carbon monoxide was observed.

EXAMPLE 11

Using the equipment and procedure described above, carbon monoxide was reacted with a medium consisting of 25 ml of methyl acetate, 113 mmols of methyl iodide, 60 mmols of lithium acetate, 20 mmols of magnesium acetate tetrahydrate, 10 mmols of nickel acetate tetrahydrate and 20 g of n-propyl sulfone, for 2 hours, at 180° C., under a total pressure of 70 bars. Upon completion of the experiment 9.2 g of acetic anhydride were determined (RY=29%).

EXAMPLE 12

Using the equipment and procedure described above, carbon monoxide was reacted with a medium consisting of 25 ml of methyl acetate, 81 mmols of methyl iodide, 40 mmols of lithium acetate, 8 mmols of nickel acetate tetrahydrate and 20 ml of tetramethylenesulfone, for 2 hours, at 180° C., under a total pressure of 40 bars.

Upon completion of the experiment, 11.8 g of acetic anhydride were determined (RY=38%).

EXAMPLE 13

Using the equipment and procedure described above, carbon monoxide was reacted with a medium consisting of 20 ml of tetramethylenesulfone, 23 ml of methyl acetate, 40 mmols of potassium acetate, 16 mmols of nickel acetate tetrahydrate and 110 mmols of methyl iodide, for 2 hours, at 200° C., under a total pressure of 70 bars.

Upon completion of the experiment, 11.3 g of acetic anhydride were determined (RY=39%).

EXAMPLE 14

Using the equipment and procedure described above, carbon monoxide was reacted with a medium consisting of 30 ml of methyl acetate, 20 ml of tetramethylenesulfone, 8 mmols of nickel acetate tetrahydrate and 120 mmols of lithium iodide, for 2 hours at 180° C., under a total pressure of 70 bars. The results obtained were as follows:
V−0.50
RY=46%
Pr=170 g/hour×liter

EXAMPLE 15

Using the equipment and procedure described above, carbon monoxide was reacted with a medium consisting of 35 ml of tetramethylenesulfone, 10 ml of methyl acetate, 8 mmols of nickel acetate tetrahydrate, 40 mmols of lithium acetate and 80 mmols of methyl iodide, for 2 hours, at 180° C., under a total pressure of 70 bars.

The results obtained were as follows:
V=0.27
RY=60%
Pr=75 g/hour×liter

EXAMPLE 16

Using the equipment and procedure described above, carbon monoxide was reacted with a medium consisting of 24 ml of methyl acetate, 20 ml of 3-methyltetramethylenesulfone, 4 mmols of nickel acetate tetrahydrate, 97 mmols of methyl iodide and 20 mmols of lithium carbonate, for 2 hours, at 180° C., under a total pressure of 70 bars.

The results obtained were as follows:
V=0.27
RY=64%
Pr=190 g/hours×liter

EXAMPLE 17

Example 3 was repeated, but the experiment was carried out under a total pressure of 170 bars.

The results obtained were as follows:
V=0.13
RY=78%
Pr=245 g/hour×liter

EXAMPLE 18

Using the equipment and procedure described above, carbon monoxide was reacted with a medium consisting of 25 ml of methyl acetate, 20 ml of tetramethylenesulfone, 40 mmols of calcium acetate hemihydrate, 80 mmols of methyl iodide, 8 mmols of nickel acetate tetrahydrate and 40 mmols of sodium iodide, for 2 hours, at 180° C., under a total pressure of 70 bars. Upon completion of the experiment, 8.9 g of acetic anhydride were determined (RY=29%).

EXAMPLE 19

Using the equipment and procedure described above, carbon monoxide was reacted with a medium consisting of 35 ml of methyl acetate, 10 ml of tetramethylenesulfone, 40 mmols of lithium acetate, 8 mmols of nickel acetate tetrahydrate and 81 mmols of methyl iodide, for 2 hours, at 180° C., under a total pressure of 70 bars.

The results obtained were as follows:
V=0.14
RY=38%
Pr=170 g/hour×liter

EXAMPLE 20

Using the equipment and procedure described above, carbon monoxide was reacted with a medium consisting of 23 ml of methyl acetate, 20 ml of tetramethylenefulfone, 16 mmols of nickel acetate tetrahydrate, 110 mmols of methyl iodide and 40 mmols of potassium acetate, for 2 hours, at 200° C., under a total pressure of 70 bars.

The results obtained were as follows:
V=0.20
RY=39%
Pr=115 g/hour×liter

EXAMPLE 21

Using the equipment and procedure described above, carbon monoxide was reacted with a medium consisting of 25 ml of methyl acetate, 20 ml of tetramethylenesulfone, 8 mmols of nickel acetate tetrahydrate, 20 mmols of methyltriphenylphosphonium iodide, 80 mmols of methyl iodide and 4 mmols of chromium hexacarbonyl, for 2 hours, at 180° C., under a total pressure of 70 bars.

The results obtained were as follows:
V=0.27
RY=43%
Pr=140 g/hour×liter

EXAMPLE 22

Example 21 was repeated, but the chromium hexacarbonyl was replaced by 40 mmols of chromium(III) acetate.

The results obtained were as follows:
V=0.43
RY=68.5%
Pr=220 g/hour×liter

EXAMPLE 23

Using the equipment and procedure described above, carbon monoxide was reacted with a medium consisting of 25 ml of methyl acetate, 20 ml of tetramethylenesulfone, 8 mmols of nickel tetracarbonyl, 80 mmols of methyl iodide and 40 mmols of lithium acetate, at 180° C., under a total pressure of 70 bars. The absorption of the carbon monoxide was complete after a reaction time of 1 hour at 180° C.; heating was nevertheless continued for an additional 1 hour.

The results obtained were as follows:
V=0.75
RY=91%
Pr=575 g/hour×liter

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a carboxylic acid anhydride, comprising carbonylating a carboxylic acid ester in liquid phase, in an essentially anhydrous reaction medium including a sulfone reaction solvent, and in the presence of a catalytically effective amount of (i) nickel and an alkyl or acyl iodide promoter therefor, and (ii) a co-catalyst which comprises at least one alkali or alkaline earth metal salt, or quaternary ammonium or phosphonium iodide.

2. The process as defined by claim 1, wherein the reactant carboxylic acid ester has the formula R—CO—OR, in which R represents an alkyl radical having at most 12 carbon atoms or a radical $C_6H_5$—$C_xH_{2x}$—, with x being an integer ranging from 1 to 6.

3. The process as defined by claim 2, wherein R is an alkyl radical having from 1 to 4 carbon atoms.

4. The process as defined by claim 3, wherein R is a methyl radical.

5. The process as defined by claim 2, wherein the sulfone reaction solvent has the formula:

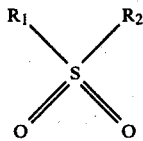

in which $R_1$ and $R_2$, which are identical or different, represent alkyl radicals having at most 4 carbon atoms, and further wherein $R_1$ and $R_2$ may together form a single divalent alkylene or alkenylene radical containing 3 to 6 carbon atoms, or such single divalent alkylene or alkenylene radical bearing 1 to 3 alkyl substituents having from 1 to 4 carbon atoms.

6. The process as defined by claim 5, wherein $R_1$ and $R_2$ together form a tetramethylene or hexamethylene radical.

7. The process as defined by claim 5, wherein $R_1$ and $R_2$ together form a single divalent alkenylene radical having 1 or 2 ethylenic double bonds.

8. The process as defined by claim 5, wherein $R_1$ and $R_2$ are identical and represent linear alkyl radicals having at most 4 carbon atoms.

9. The process as defined by claim 5, wherein the sulfone reaction solvent is tetramethylenesulfone, 3-methyltetramethylenesulfone, 2,4-dimethyltetramethylenesulfone, or mixtures thereof.

10. The process as defined by claim 5, wherein the sulfone reaction solvent comprises at least 10% by volume of the reaction medium.

11. The process as defined by claim 10, wherein the sulfone reaction solvent comprises from 20 to 75% by volume of the reaction medium.

12. The process as defined by claim 10, wherein the co-catalyst is a quaternary ammonium or phosphonium iodide respectively having the structural formula:

$$R_3N^+(R_4)_3 \qquad \text{(III)}$$

$$R_3P^+(R_4)_3 \qquad \text{(IV)}$$

in which $R_3$ and $R_4$, which are identical or different, represent linear alkyl radicals having at most 4 carbon atoms, and further wherein $R_4$ may be phenyl, tolyl or xylyl.

13. The process as defined by claim 10, wherein the co-catalyst is an alkali metal salt or alkaline earth metal salt having the formula:

$$M_b{}^{a+}X_c{}^{m-}$$

in which a, m, b and c are integers equal to 1 to 2, the respective values of which being such as to satisfy the condition $a \times b = m \times c$, and, if a and m are identical, b and c are equal to 1, M represents a lithium, sodium, potassium, cesium, rubidium, calcium or magnesium atom and $X^{m-}$ is $OH^-$, $Cl^-$, $Br^-$, $I^-$, $CO_3{}^=$, $NO_3{}^-$, $R''$—$O^-$ or $R''$—$CO$—$O^-$, with $R''$ being defined as was R and further wherein $R''$ and R may be identical or different.

14. The process as defined by claim 13, wherein the co-catalyst is a lithium, sodium or potassium salt.

15. The process as defined by claims 13 or 14, wherein the co-catalyst is an iodide.

16. The process as defined by claims 13 or 14, wherein the co-catalyst is a carboxylate.

17. The process as defined by claim 16, wherein the co-catalyst is an acetate.

18. The process as defined by claims 12 or 13, wherein the reaction is carried out in the presence of an alkyl or acyl iodide respectively having the formula R'I and R'COI, in which R' is defined as was R, and further wherein R' and R may be identical or different.

19. The process as defined by claim 18, wherein the reaction is carried out in the presence of an alkyl iodide having at most 4 carbon atoms.

20. The process as defined by claim 19, said alkyl iodide being formed in situ from an alkali or alkaline earth metal iodide.

21. The process as defined by claims 12 or 13, wherein the reaction is carried out in the presence of 5 to 2,000 milligram atoms of nickel per liter of reaction medium.

22. The process as defined by claim 21, wherein the molar ratio I/Ni ranges from 1 to 100.

23. The process as defined by claim 22, wherein the molar ratio of the co-catalyst to the nickel ranges from 0.5 to 50.

24. The process as defined by claim 23, wherein the reaction temperature is in excess of 160° C.

25. The process as defined by claim 24, wherein the total reaction pressure ranges from 15 to 700 bars.

26. The process as defined by claim 21, the reaction being carried out in the presence of 20 to 1,000 milligram atoms of nickel per liter of reaction medium.

27. The process as defined by claim 22, the molar ratio I/Ni ranging from 3 to 50.

28. The process as defined by claim 23, the molar ratio of the co-catalyst to the nickel ranging from 2 to 25.

29. The process as defined by claim 24, the reaction temperature ranging from 180° to 220° C.

30. The process as defined by claim 25, the total reaction pressure ranging from 25 to 200 bars.

* * * * *